United States Patent [19]

Nelson et al.

[11] 4,308,217
[45] Dec. 29, 1981

[54] DISULFIDES OF AMIDES OF PHOSPHORIC ACID

[75] Inventors: Stephen J. Nelson, Galesburg; Clifford E. Sacks, Portage, both of Mich.

[73] Assignee: The Upjohn Company, Kalamazoo, Mich.

[21] Appl. No.: 151,558

[22] Filed: May 20, 1980

[51] Int. Cl.³ .............................................. C07F 9/24
[52] U.S. Cl. .............................. 260/927 R; 260/968; 260/937
[58] Field of Search .......................... 260/92 G, 927 R

[56] References Cited
PUBLICATIONS

Alimov et al. "Isvestiya Akedemii Nauk, Otdelenie Kimi Cheskikh Nauk," No. 6, pp. 1132–1134 (6/1963).

Primary Examiner—Anton H. Sutto
Attorney, Agent, or Firm—Joan Thierstein

[57] ABSTRACT

Selected disulfides of various amides of phosphoric acids are claimed. They are useful to make corresponding sulfenyl chlorides or bromides in novel processes for preparing phosphorus derivatives of aminothiomethylcarbamates useful as pesticides.

32 Claims, No Drawings

DISULFIDES OF AMIDES OF PHOSPHORIC ACID

DESCRIPTION

Brief Summary of the Invention

This invention pertains to novel processes for preparing phosphorus derivatives of aminothiomethylcarbamates. These carbamates are known to be useful as pesticides. The invention is particularly directed to the use of a product which is prepared by a reaction of a disulfide of various amides of phosphoric acids with chlorine or bromine. The product includes previously shown sulfenyl chlorides of various amides of phosphoric acids for use as intemediates in a process to make the pesticides. The reaction preparing the sulfenyl chloride or bromide product for use herein is novel. Further, the preparation of sulfenyl chlorides or bromides according to the instant case is unexpectedly advantageous and therefore unobvious over the prior art. Finally, the disulfides of the invention include selected compounds which insofar as is presently known, no one has previously prepared.

Background of the Invention

N-[(phosphinyl)amino]thio- and N-[(phosphinothioyl)amino]thiomethylcarbamates, a process for preparation and formulations of them suitable for pesticidal use are shown in U.S. Pat. No. 4,081,536, issued Mar. 28, 1978. Phosphoroaminosulfenyl derivatives of benzofuran carbamates and preparation thereof are disclosed in U.S. Pat. No. 4,024,277, issued Mar. 17, 1977. Additional N-[(phosphinyl or phosphinothioyl)amino]thiomethylcarbamates and pesticidal methods for use thereof are disclosed in U.S. application Ser. No. 962,266, filed Nov. 20, 1978 now U.S. Pat. No. 4,208,409. These phosphorus acid derivatives of aminothiomethylcarbamate pesticides are among the compounds prepared by the novel processes of the present invention and, therefore, the above patents and application can be referred to for relevant status of the art.

Other prior art includes a review by E. Kühle, "One Hundred Years of Sulfenic Acid Chemistry I: Sulfenyl Halide Syntheses", Synthesis International Journal of Methods in Synthetic Organic Chemistry, No. 11, pp. 561–580 (November, 1970) and a disulfide preparation by M. V. Kalnins, "Reactions of Phthalimide and Potassium Phthalimide with Sulfur Monochloride", Can. J. Of Chem. Vol. 44, pp. 2111–2113 (1966). Although the review discloses numerous sulfenyl halides prepared by halogenation of organic disulfide, no compounds containing the phosphorus nitrogen sulfur linkage of the present invention are shown. Likewise, although Kalnins' discloses disulfides, the P-N-S linkage is not shown. The references P. I. Alimov, et al., "Derivatives of Diethoxyphosphorylamido-N-Sulfenic Acid", Bulletin of the Academy of Sciences of the USSR, Division of Chemical Science, English Edition, pp. 1220–1221 (1964), translated from Izvestiya Akademii Nauk SSSR, Seriya Khimicheskaya No. 7, pp. 1316–1317 (July, 1964) and P. I. Alimov, et al., "Synthesis of Some N-Sulfene Derivatives of the Amide of Diethylphosphoric Acid", Bulletin of the Academy of Science of the USSR, Division of Chemical Science, English Edition, pp. 1034–1036 (1964), translated from Izvestiya Akedemii Nauk, Otdelenie Khimicheskikh Nauk, No. 6, pp. 1132–1134 (June 1963) are also relevant. These references show the preparation of N-(sulfenechloro)ethylamide of diethylphosphoric acid and its reaction with simple amines and alcohols. However, contrary to the present invention the preparation is accomplished by the action of sulfuryl chloride on a disulfide precursor. A similar preparation using sulfuryl chloride is shown in U.S. Pat. No. 4,024,277 cited above.

The Alimov, et al. references disclose a limited number of disulfide species. Further, U.S. Pat. No. 4,024,277 shows a process which appears to prepare additional disulfides. However, selected disulfides of the present invention are novel compounds not taught by these references.

Further background teaching phosphoramide reactants denoted as Formula V herein is found in Methoden der Organischen Chemie (Houben-Weyl) Volume 12, part 2, pages 610, 760 (thiophosphoramides) and pages 276, 413 (phosphoramides) George Thieme Verlag (Pub.), Stuttgart, Germany, 1963. In addition, L. Anschütz, et al. Ber. 61, 1264 (1928) teaches a benzothiophosphol chloride from which the corresponding amides of this invention can be made.

DETAILED DESCRIPTION OF THE INVENTION

The present invention is a process for preparing compounds having the formula

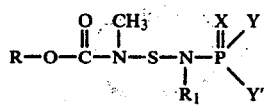

wherein R is selected from the group consisting of

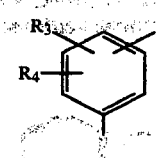

a.

wherein $R_2$, $R_3$ and $R_4$ are the same or different and are selected from the group consisting of hydrogen, lower alkyl of one to five carbon atoms, inclusive, halogen, lower alkoxy of one to five carbon atoms, inclusive, lower alkylthio of one to five carbon atoms, inclusive, dialkylamino with each alkyl the same or different and having one to three carbon atoms, inclusive, and $N=CHN(CH_3)_2$;

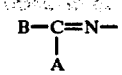

b.

wherein A and B are the same or different and are selected from the group consisting of lower alkyl of one to five carbon atoms, inclusive, lower alkylthio of one to five carbon atoms, inclusive, phenylthio wherein phenyl is unsubstituted or substituted with one to three substituents, same or different, selected from the group consisting of halogen and lower alkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when A is hydrogen, B is of the formula:

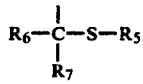

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula:

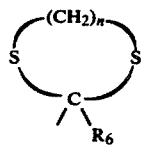

wherein n is 2 or 3 and the alkylene portion of the ring is unsubstituted or substituted with one or two methyl groups; A and B taken together with the carbon atom to which they are attached form a dithio heterocyclic of the formula:

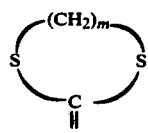

wherein m is 2 or 3 and the alkylene portion of the ring is unsubstituted or substituted with one to two methyl groups, and

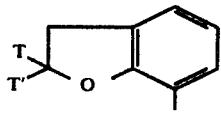

wherein T and T' can be the same or different and are selected from the group consisting of hydrogen and lower alkyl of from one to six carbons; $R_1$ is selected from the group consisting of lower alkyl, phenyl, substituted phenyl, phenyl lower alkyl, and cycloalkyl; X is oxygen or sulfur; Y and Y' are the same or different and are selected from the group consisting of $Y_1$ and $R_1'$     $I_1$ and Y and Y' taken together to form a functionality selected from the group consisting of:

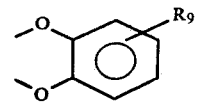

I'

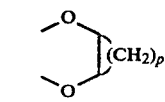

I'' and

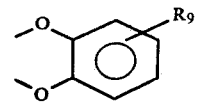

I''' wherein $Y_1$ and $Y_1'$ are selected from the group consisting of lower alkyl, lower alkoxy, lower alkylthio, cycloalkyl, phenyl, substituted phenyl, phenoxy, substituted phenoxy, thiophenoxy, and substituted thiophenoxy; $Z_1$ through $Z_6$ are the same or different and are selected from the group consisting of hydrogen, methyl and ethyl; and k is 0 or 1, p is three or four and $R_9$ is selected from the group consisting of hydrogen, lower alkyl, lower alkoxy and halogen; which comprises:

(step 1) reacting a compound having the formula

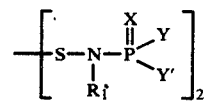

V wherein $R_1$, X, Y, and Y' are as defined above with chlorine or bromine and (step 2) reacting the product of the step 1 reaction with a compound having the formula ROC(O)N(CH$_3$)H wherein R is the same as above.

Compounds of formula V above are referred to herein as disulfides. The disulfides useful in the present invention include selected compounds which are novel. These compounds have the formula

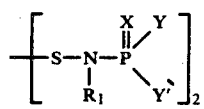

V' wherein $R_1$ and X are as defined above, and Y and Y' are limited to substituents wherein Y and Y' are taken together to form a functionality selected from the group consisting of

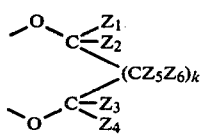

I'

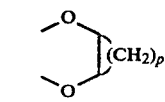

I'' and

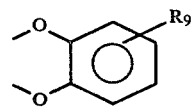

I''' wherein $Z_1$ through $Z_6$, k, p, and $R_9$ are as described above. None of the above cited prior art references teach the novel disulfides of the present invention, In the foregoing designation of variables, "lower alkoxy" means methoxy, ethoxy, propoxy, isopropoxy, butoxy, pentoxy, and the further isomeric forms thereof. Likewise, "lower alkylthio" means methylthio, ethylthio, propylthio, isopropylthio, butylthio, pentylthio, and further isomeric forms thereof.

"Lower alkyl" means methyl, ethyl, propyl, butyl, pentyl, and the isomeric forms thereof; while "cycloalkyl" means cyclopropyl, cyclobutyl, cyclopentyl, cyclohexyl optionally substituted with methyl, ethyl and propyl to a total of nine carbon atoms.

"Phenlower alkyl" means benzyl, phenethyl, phenpropyl, phenbutyl, phenpentyl and isomeric forms thereof.

"Substituted phenyl" means lower alkyl, lower alkoxy, halogen, nitro, and cyano-substituted-phenyl. There can be combinations of substituents such as 4-propyl-2-methyl, 2-chloro-4-methyl, 3,4-diethoxy, 3-cyano-4-ethoxy-phenyl. Practically speaking, the "substituted phenyl" group is limited to a total of ten carbon atoms, e.g., 4-isobutylphenyl.

"Substituted phenoxy" means lower alkyl, lower alkoxy, halogen, nitro and cyano substituted phenoxy. There can be combinations of substituents such as 4-propyl-2-methyl, 2-chloro-4-methyl, 3,4-diethoxy, 3-cyano-4-ethoxy, and the like. The substituted phenoxy is limited to a total of ten carbon atoms, e.g., 4-isobutylphenoxy.

"Substituted thiophenoxy" means lower alkyl, lower alkoxy, halogen, nitro, and cyano substituted thiophenoxy. There can be combinations of substituents such as 4-propyl-2-methyl, 2-chloro-4-methyl, 3,4-diethoxy. The substituted thiophenoxy is limited to a total of ten carbon atoms, e.g., 4-isobutylthiophenoxy.

The novel disulfides of this reaction are generally prepared by reacting sulfur monochloride with a phosphoramide having the formula

wherein Y and Y' are limited to the definitions of Y and Y' taken together to form a functionality selected from the group consisting of I', I" and I''' as shown above.

Preparation of these disulfides is accomplished by treating a solution of a corresponding phosphoramide and a tertiary amine, such as triethylamine, with sulfur monochloride. Solvents are acetonitrile and tetrahydrofuran, preferably acetonitrile. The temperature of the treatment is from $-20°$ to $+50°$ C., preferably $0°$ C. Cooling to about $-20°$, filtering and washing with water gives a good yield of high purity disulfides.

The invention is also directed to preparation of sulfenyl chlorides or bromides of phosphoramide solution prepared by a novel process. The process is recited above as step 1 in which a disulfide V is reacted with chlorine or bromine. The resulting sulfenyl halide compounds have the formula

wherein $R_1$, X, Y, and $Y_1$ are as defined above and Q is chlorine or bromine. Due to instability of these sulfenyl halides II when isolated complete physical and chemical data are difficult to obtain. However, NMR spectra and analysis of the pesticide made by reacting a sulfenyl chloride II with $ROC(O)N(CH_3)H$ in step 2 described above are both consistent with the conclusion that these compounds have formula II described herein.

Generally, step 1 and step 2 as set forth above are carried out in the following manner.

In step 1 a disulfide compound having the formula V in an inert solvent is reacted with chlorine or bromine. The solvent is any inert solvent, preferably acetonitrile, hexane, dichlormethane, or tetrahydrofuran. Although step 1 can be performed as an independent step, the step 1 solvent may preferably be one that can be used in the subsequent step 2 reaction as described herein. The chlorine may be added to the disulfide solution in the form of a gas and the bromine in the form of a liquid. Since the resulting chloro containing compounds are preferred, chlorine gas is the preferred cleveage agent for the disulfide in this reaction. This reaction may be carried out at temperatures from $-40°$ to $+25°$ C., preferably $-30°$ C. to $-10°$ C. However, when using chlorine gas the suggested temperature range is from $-30°$ to $+25°$ C., preferably from $-20°$ to $-10°$ C. The product resulting from this reaction may be used directly in the step 2 reaction described above if an appropriate solvent is present. Alternatively, the solvent useful in step 1 may be removed and substantially replaced by known methods with an appropriate solvent for the step 2 reaction. Preferred conditions for such replacement are low temperature and pressure in a nitrogen atmosphere.

In step 2 the sulfenyl halide product of step 1 is reacted with the amide compound, $ROC(O)N(CH_3)H$. The reaction is effected in the cold, preferably $-20°$ to $+25°$ C., in the presence of a suitable acid acceptor and an inert organic medium. Illustrative of suitable acid acceptors are trialkyl amine, (e.g., triethylamine) pyridine and lutidine. Illustrative of the organic media for the reaction are dimethylformamide, diethylether, hexane, tetrahydrofuran, methylenechloride and acetonitrile, the preferred media being tetrahydrofuran. Cuprous chloride and aluminum chloride may be used to catalyze the reaction. Cuprous chloride is the preferred catalyst.

The desired compounds according to Formula I are recovered and purified according to conventional methods. Filtration, solvent evaporation, chromatography, crystallization, and combinations thereof are employed. Some of the compounds are obtained as crystals while others are purified as oils.

This invention includes unexpected advantages over that known in the art. The advantages are shown above in the step 1 reaction with disulfides. The disulfide reaction with chlorine or bromine is novel and results in unexpectedly improved yields of the sulfenyl halides II. Therefore, improved yields of desired pesticides are obtained when compounds II are reacted with the compounds having the formula $ROC(O)N(CH_3)H$, as shown by step 2 above. In fact, yields indicate nearly a stoichiometric reaction between sulfenyl chlorides in the solution obtained in step 1 and the compound $ROC(O(N)CH_3)H$ in step 2. For comparision, the use of sulfur dichloride and sulfuryl chloride in analogous preparations of corresponding sulfenyl chlorides are disclosed in U.S. Pat. No. 4,081,536, U.S. Pat. No. 4,024,277, U.S. application Ser. No. 962,266, and the Alimov, et al. references discussed above. The sulfenyl chloride in solution made by these prior art preparations reacts with only about one half the expected amount of compounds of formula ROC(O)N(CH₃)H when used in a coupling step 2 reaction similar to that shown herein. Therefore, the process of step 1 in this invention is unexpectedly advantageous and unobvious.

Another disadvantage of one of the above noted prior art methods is that the desired pesticide decomposes in the presence of sulfur dichloride. In other words, if sulfur dichloride is used to make a sulfenyl chloride for use in the further reaction to the desired pesticide, intervening steps are required to thoroughly remove residual sulfur dichloride before proceeding to the further reaction.

Therefore, in summary it is now found that the generation of a product having the formula II noted above by a heretofore unknown reaction process shown in step 1 in which a compound having the formula V is reacted with chlorine or bromine and further coupling with a compound ROC(O)N(CH₃)H shown in step 2 is unexpectedly advantageous. For example, improved yields result. Furthermore, selected disulfides useful herein are novel.

The following examples illustrate each novel aspect of this invention and at the same time demonstrate the total process for the preparation of a desired pesticide I. However, these examples should not be considered limiting as to the use of any particular part of the invention process.

Starting materials for use in the present invention are known, available or can be prepared by methods described in the prior art.

The definitions and explanations below are for the terms as used throughout the entire patent application including both the specification and claims.

g Refers to grams, Kg refers to kilograms, gal refers to gallons, mol refers to mole, ml refers to milliliter, l refers to liters, C refers to carbon, NMR refers to nuclear magnetic resonance, mp refers to melting point, mass spec. refers to mass spectrometry, mmol refers to millimole, TLC refers to thin-layer chromatography.

Preparation
I—N,N'-dithiobis[N-(1-methylethyl)-1,3,2-dioxaphosphorinan-2-amino]-2,2'-disulfide $V_1'$

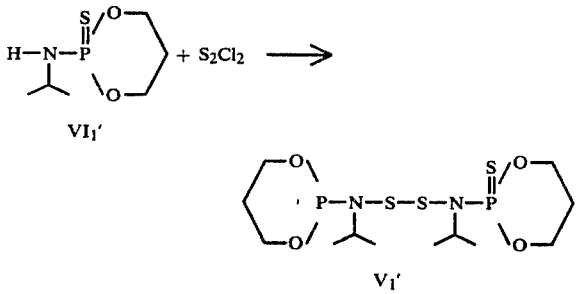

$VI_1'$ $V_1'$

Phosphoramide $VI_1'$ (19.0 g, 0.097 mol) and triethylamine (14.7 ml, 0.11 mol) are dissolved in tetrahydrofuran (50 ml) and cooled to 0° C. S₂Cl₂ (sulfur monochloride) (4.3 ml, 0.053 mol) in tetrahydrofuran (50 ml) is added over 40 minutes with stirring. The temperature reaches 5° C. during the addition and a voluminous white precipitate forms. After an additional 30 minutes, 200 ml of H₂O (water) is added and the solids are filtered. The filter cake is washed two times with 30 ml of water each time and one time with 50 ml of ice cold acetone to give a white powder which is dried in a vacuum oven at 60° C. for 10 hours. N,N'-dithiobis[N-(1-methylethyl)-1,3,2-dioxaphosphorinan-2-amine]2,2'-disulfide $V_1'$ is obtained in the following yield: 17.4 g (80 percent); mp. 148.5-151. TLC: 25 percent ethyl acetate/hexane; $R_f=0.16$. Analytical data is:

NMR: δ=1.26 d, J=6.66 Hz (12H); 1.67–2.50 m (4H); 4.10–4.70 m (10H).

$R_f$: 60% ethylacetate/hexane-0.56.
$R_f$: 30% ethylacetate/hexane-0.18.
mp: 150–152 (acetone).

C and H: Calc. C, 31.85; H, 5.79; N, 6.19; P, 13.69; S, 28.34. Found: C, 31.94; H, 5.70. N, 6.19; P, 13.75; S, 28.28.

Mass Spec: M+, 452; M-194, 258; M-226, 226; M-258, 194.

Preparation
II—N,N'-dithiobis[5,5-dimethyl-N-(1,1-dimethylethyl)-1,3,2-dioxaphosphorinan-2-amine], 2,2'-disulfide $V'_2$

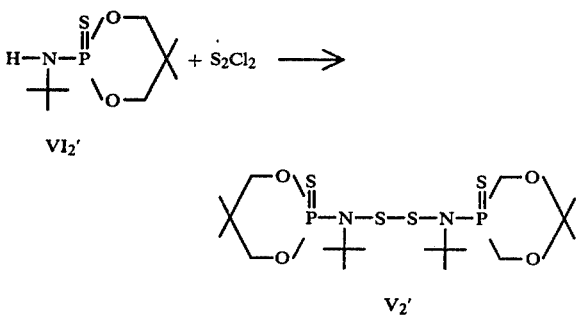

$VI_2'$ $V_2'$

Phosphoramide $VI_2'$ (161.9 Kg, 682 mol) and triethylamine (77.7 Kg, 769 mol) are dissolved in tetrahydrofuran (169.2 l) and cooled to 0° C. S₂Cl₂ (sulfur monochloride) (45.9 Kg, 340 mol) is added over 40 minutes with stirring. The temperature reaches 5° C. during the addition and a voluminous white precipitate forms. After an additional 30 minutes the temperature is reduced to −20° C. and the solids are filtered. The filter cake is washed two times with 50 gal of water each time and one time with 20 gal. of ice cold acetonitrile to give a white powder which is dried in a vacuum oven at 45° C. for 2 days. N,N'-dithiobis[5,5-dimethyl-N-(1,1-dimethylethyl)-1,3,2-dioxaphosphorinan-2-amine]2,2'-disulfide $V'_2$ is obtained in the following yield: 148 Kg (276 mol), 81 percent. Analytical data is summarized as follows: mp 152–154, TLC 20 percent ethylacetate/hexane $R_f=0.6$.

Appropriate phosphoramide VI starting materials are substituted in reactions similar to Preparation I and II according to the process as described herein to prepare corresponding novel intermediates V' of the invention as follows:

N,N'-dithiobis[5,5-diethyl-N-(1-methylethyl)-1,3,2-dioxaphosphorinan-2-amine], 2,2'-disulfides;
N,N'-dithiobis[5,5-dimethyl-N-ethyl-1,3,2-dioxaphosphorinan-2-amine], 2,2'-disulfide;
N,N'-dithiobis[N-(1-methylethyl)-1,3,2-dioxaphospholan-2-amine], 2,2'-disulfide;
N,N'-dithiobis[4,4,6-trimethyl-N-(1-methylethyl)-1,3,2-dioxaphosphorinan-2-amine], 2,2'-disulfide;
N,N'-dithiobis[5,5-diethyl-N-cyclohexyl-1,3,2-dioxaphosphorinan-2-amine], 2,2'-disulfide;
N,N'-dithiobis[5,5-dimethyl-N-cyclohexyl-1,3,2-dioxaphosphorinan-2-amine], 2,2'-disulfide;

N,N'-dithiobis[N-methyl-1,3,2-dioxaphosphorinan-2-amine], 2,2'-disulfide;
N,N'-dithiobis[hexahydro-N-cyclopentyl-1,3,2-benzodioxaphosphol-2-amine], 2,2'-disulfide;
N,N'-dithiobis[N-(2-methylpropyl)-1,3,2-benzodioxaphosphol-2-amine], 2,2'-disulfide.

Examples of the novel product or solution of the invention which is believed to contain sulfenyl chlorides II shown by step 1 above is illustrated by the following Examples A and B.

EXAMPLE A

N,N'-dithiobis[N-(1-methylethyl)-1,3,2-dioxaphosphorinan-2-amine], 2,2'-disulfide V₁' from Preparation I (3.09 g, 6.8 mmol) is stirred with dichloromethane (9 ml) and cooled to 0° C. Cl₂ (chlorine) gas is sparged into the suspension until TLC indicates complete consumption of disulfide. A mild exotherm occurs during the sparging with the final temperature reaching 5° C. The resulting yellow, homogeneous solution may be used directly or the dichloromethane can be replaced with tetrahydrofuran which is the preferred solvent of the subsequent step 2 reaction of the present invention.

The active compound resulting from Example A is [(1-methylethyl)(2-thio-1,3-dioxa-2-phosphocyclohex-2-yl)amino]sulfenyl chloride II₁.

EXAMPLE B

N,N'-dithiobis[5,5-dimethyl-N-(1,1-dimethylethyl)-1,3,2-dioxaphosphorinan-2-amine], 2,2'-disulfide V'₂ from Preparation II (400 mg, 0.745 mmol) is suspended in 2 ml carbon tetrachloride and cooled in an ice-methanol bath at −10°. Chlorine in carbon tetrachloride (1.82 M, 0.41 ml, 0.75 mmol) is added over three minutes during which time the mixture becomes homogeneous. The pmr spectrum of this solution shows significant changes from the spectrum of the disulfide. No significant change in the spectrum occurs on standing 16 hours at room temperature.

PMR (CDCl₃, TMS)

Disulfide—4.45–3.20 (M, 8H, —OCH₂), 1.56 (s, 18H N—C(CH₃)₃), 1.23

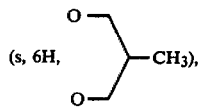

(s, 6H, )—CH₃), 0.83

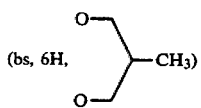

(bs, 6H, )—CH₃)

sulfenyl chloride—4.10

(dd, 4H, O—CH₂), 1.66 (s, 9H, N-C(CH₃)₃), 1.16

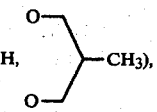

(s, 3H, )—CH₃), 1.12

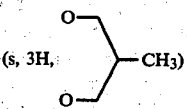

(s, 3H, )—CH₃)

m=multiplet, s=singlet, bs=broad singlet, dd=doublet of doublets.

Thus, the active compound resulting from Example B is [1,1-dimethylethyl)(2-thio-1,3-dioxa-2-phosphocyclohex-2-yl)amino]sulfenyl chloride II'₂.

Appropriate disulfide V starting materials are substituted in Examples A and B according to the process as described herein to prepare corresponding novel products or solutions of the process. The disulfide V includes those selected novel compounds V' named above as well as other disulfides included in the above noted generic scope shown as step 1.

Likewise, other chlorine or bromine generating agents named herein are substituted for chlorine gas in Examples A and B according to the process as described herein to prepare similar chlorine or bromine containing products respectively.

Examples I and II provide experimental descriptions showing the above step 2 in which the desired pesticide I is obtained.

EXAMPLE I

Preparation of methyl N-[[[methyl[[(1-methylethyl)(2-thioxo-1,3,2-dioxaphosphorinan-2-yl)amino]thio]amino]carbonyl]oxy]ethanimidothioate, I₁'

A solution from Example A above (13.6 mmol) in dichloromethane (9 ml) is added to an emerald green colored solution of methyl-[[(methylamino)carbonyl]oxy]ethanimidothioate hereinafter named methomyl (2.05 g, 12.6 mmol) triethylamine (2.0 ml, 14.5 mmol) and CuCl (cuprous chloride) (0.062 g, 0.63 mmol) in tetrahydrofuran (15 ml) at 0° over five minutes. A precipitate develops and the reaction color changes to olive green. After 45 minutes the reaction is filtered and the filter cake (triethylamine hydrochloride plus product) is washed one time with hexane and three times with water. The white solid is dried 12 hours at 40° C. under vacuum to yield 2.0 g (40 percent) of product. The mother liquor contains another 1.1 g of product isolated by flash chromatography (60 percent ethyl acetate/hexane). The product yield is 62 percent; mp. 137–139 (low) of methyl N-[[[methyl[[(1-methylethyl)(2-thioxo-1,3,2-dioxaphosphorinan-2-yl)amino]thio]amino]carbonyl]oxy]ethanimidothioate I₁'.

In other words, the product generated by Example A above reacted in almost stoichiometric ratio with methomyl in tetrahydrofuran containing CuCl (cuprous chloride) (0.05 equiv.) and triethylamine to give 40 percent yield crystallized directly from the reaction mixture.

EXAMPLE II

Preparation of methyl N-[[[methyl[[(1,1-dimethylethyl)(5,5-dimethyl-2-thioxo-1,3,2-dioxaphosphorinan-2-yl)amino]thio]amino]carbonyl]oxy]ethanimidothioate $I_2'$ A solution from Example B above (0.019 mmol) in tetrahydrofuran (25 ml) is added to an emerald green colored solution of methomyl (2.3 g, 0.014 mol), triethylamine (2.8 ml, 0.020 mol) and CuCl (cuprous chloride) (0.071 g, 0.72 mmol) in tetrahydrofuran (5 ml) at 3° over five minutes. A precipitate develops and the reaction color changes to olive green. After 45 minutes the reaction is filtered and the filter cake (triethylamine hydrochloride plus product) is washed one time with cold tetrahydrofuran (20 ml) and three times with 30 ml of water. The white solid is dried 12 hours at 30° C. (under vacuum to yield 4.72 g) (76 percent) of the product N-[[[methyl[[(1,1-dimethylethyl)(5,5-dimethyl-2-thioxo-1,3,2-dioxaphosphorinan-2-yl)amino]thio]amino]carbonyl]oxy]ethanimidothioate $I_2'$., mp 163°-166° C.

Likewise, the product generated by Example B above reacted in almost stoichiometric ratio with methomyl in tetrahydrofuran containing CuCl (cuprous chloride and triethylamine).

Finally, appropriate products, prepared according to general processes as described herein in step 1 by substituting corresponding disulfides V in Examples A and B, are thereinafter substituted in Examples I and II according to the process as described herein as step 2. Corresponding desired pesticides of formula I are thereby obtained.

We claim:

1. A compound having the formula

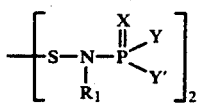

V wherein X is oxygen or sulfur; $R_1$ is lower alkyl, phenyl, substituted phenyl, phenyl lower alkyl or cycloalkyl; Y and Y' taken together for a functionality selected from the group consisting of

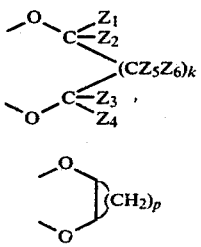 I'

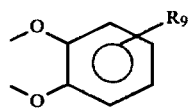 I'' and

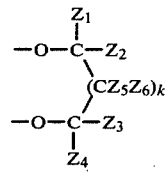 I''' wherein $Z_1$ through $Z_6$ are the same or different and are hydrogen, methyl or ethyl, and k is 0 or 1; p is three or four, and $R_9$ is hydrogen, lower alkyl, lower alkoxy or halogen.

2. A compound according to claim 1 wherein Y and Y' are $$\begin{array}{c} Z_1 \\ | \\ -O-C-Z_2 \\ \diagdown \\ (CZ_5Z_6)_k \\ \diagup \\ -O-C-Z_3 \\ | \\ Z_4 \end{array} \quad I'$$

wherein $Z_1$ through $Z_6$ and k are the same as defined in claim 1.

3. A compound according to claim 2 wherein X is sulfur.

4. A compound according to claim 2 wherein X is oxygen.

5. A compound according to claim 2 wherein $Z_1$ through $Z_6$ are hydrogen.

6. A compound according to claim 3 wherein k is 1; $Z_5$ and $Z_6$ are lower alkyl.

7. A compound according to claim 3 wherein k is 1, and $Z_1$ through $Z_6$ are hydrogen.

8. A compound according to claim 3 wherein k is 1; $Z_2$, $Z_3$ and $Z_4$ are lower alkyl.

9. A compound according to claim 6 wherein $R_1$ is lower alkyl.

10. A compound according to claim 7 wherein $R_1$ is lower alkyl.

11. A compound according to claim 8 wherein $R_1$ is lower alkyl.

12. A compound according to claim 6 wherein $R_1$ is cycloalkyl.

13. A compound according to claim 9, N,N'-dithiobis[5,5-dimethyl-N-(1-methylethyl)-1,3,2-dioxaphosphorinan-2-amino], 2,2'-disulfide.

14. A compound according to claim 9, N,N-dithiobis[5,5-dimethyl-N-1,1-dimethylethyl-1,3,2-dioxaphosphorinan-2-amine], 2,2'-disulfide.

15. A compound according to claim 9, N,N'-dithiobis[5,5-diethyl-N-(1-methylethyl)-1,3,2-dioxaphosphorinan-2-amine], 2,2'-disulfide.

16. A compound according to claim 9, N,N'-dithiobis[5,5-dimethyl-N-ethyl-1,3,2-dioxaphosphorinan-2-amine], 2,2'-disulfide.

17. A compound according to claim 5, bis[isopropyl-N,N'-dithiobis[N-(1-methylethyl)-1,3,2-dioxaphospholan-2-amine], 2,2'-disulfide.

18. A compound according to claim 5, N,N'-dithiobis[N-(1-methylethyl)-1,3,2-dioxaphosphorinan-2-amine], 2,2'-disulfide.

19. A compound according to claim 11, [N,N'-dioxaphosphorinan-2-amine], 2,2'-disulfide.

20. A compound according to claim 12, N,N'-dithiobis[5,5-diethyl-N-cyclohexyl-1,3,2-dioxaphosphorinan-2-amine], 2,2'-disulfide.

21. A compound according to claim 12, N,N'-dithiobis[5,5-dimethyl-N-cyclohexyl-1,3,2-dioxaphosphorinan-2-amine], 2,2'-disulfide.

22. A compound according to claim 5, N,N'-dithiobis[N-methyl-1,3,2-dioxaphosphorinan-2-amine], 2,2'-disulfide.

23. N,N'-dithiobis[N-(1-methylethyl)-1,3,2-dioxaphosphorinan-2-amine], 2,2'-disulfide.

24. N,N'-dithiobis[5,5-dimethyl-N-(1-methylethyl)-1,3,2-dioxaphosphorinan-2-amine], 2,2'-disulfide.

25. A compound according to claim 1 wherein Y and Y' are

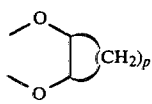

wherein p is three or four.

26. A compound according to claim 25 wherein X is sulfur.

27. A compound according to claim 25 wherein X is oxygen.

28. A compound according to claim 27, N,N'-dithiobis[hexahydro-N-cyclopentyl-1,3,2-benzodioxaphosphol-2-amine], 2,2'-dioxide.

29. A compound according to claim 1 wherein Y and Y' are

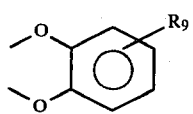

wherein $R_9$ is the same as defined in claim 7.

30. A compound according to claim 29 wherein X is sulfur.

31. A compound according to claim 29 wherein X is oxygen.

32. A compound according to claim 30, N,N'-dithiobis[N-(2-methylpropyl)-1,3,2-benzodioxaphosphol-2-amine], 2,2'-disulfide.

* * * * *